United States Patent [19]

Barone et al.

[11] 4,283,307

[45] Aug. 11, 1981

[54] CATALYST STRUCTURE FOR THE PARTIAL OXIDATION OF N-BUTANE TO PRODUCE MALEIC ANHYDRIDE

[75] Inventors: Bruno J. Barone, Houston; Gaylon T. Click, Pearland, both of Tex.

[73] Assignee: Denka Chemical Corporation, Houston, Tex.

[21] Appl. No.: 155,556

[22] Filed: Jun. 2, 1980

[51] Int. Cl.³ .. B01J 23/22; B01J 27/18; B01J 35/00
[52] U.S. Cl. .................................. 252/432; 252/435; 252/437; 252/477 R; 260/346.75
[58] Field of Search ............ 252/432, 435, 437, 477 R

[56] References Cited

U.S. PATENT DOCUMENTS

| 2,078,945 | 5/1937 | Houdry | 252/454 |
|---|---|---|---|
| 2,408,164 | 9/1946 | Foster | 252/467 |
| 2,478,194 | 8/1949 | Houdry | 252/477 R |
| 3,798,176 | 3/1974 | Ao | 252/437 |
| 3,848,033 | 11/1974 | Callahan et al. | 264/13 |
| 3,985,775 | 10/1976 | Harrison | 252/435 X |
| 4,153,539 | 5/1979 | Herrington et al. | 252/477 R |
| 4,178,298 | 12/1979 | Stefani et al. | 260/346.75 |

*Primary Examiner*—W. J. Shine
*Attorney, Agent, or Firm*—Kenneth H. Johnson

[57] ABSTRACT

Phosphorus-Vanadium oxidation catalyst prepared as tablets with a hole in the center produce higher yields of maleic anhydride from $C_4$'s, particularly n-butane than the same catalyst without the hole.

9 Claims, 3 Drawing Figures

CATALYST STRUCTURE FOR THE PARTIAL OXIDATION OF N-BUTANE TO PRODUCE MALEIC ANHYDRIDE

BACKGROUND OF THE INVENTION

1. Field of the Invention

The present invention relates to an improved catalyst structure for use in the partial oxidation of hydrocarbons to prepare dicarboxylic acids and anhydrides.

2. Prior Art

Basically, all of the methods for producing catalysts for maleic anhydride production employ vanadium in a valence state of less than +5. One method of achieving this is to begin with vanadium in less than the +5 valence state. Another method and that used most widely in the art is to start with vanadium in the +5 state and reduce the valency to less than +5.

Usually the reduced vanadium has been obtained by reducing $V_2O_5$ in a solution with HCl to obtain vanadyl chloride. A typical catalyst preparation may involve dissolving the vanadium, phosphorus, and other components in a common solvent, such as hot hydrochloric acid and thereafter depositing the solution onto a carrier. The reduced vanadium with a valence of less than 5 is obtained by initially using a vanadium compound with a valence of plus 5 such as $V_2O_5$ and thereafter reducing to the lower valence with, for example, hydrochloric acid during the catalyst preparation to form the vanadium oxysalt, vanadyl chloride, in situ. The vanadium compound is dissolved in a reducing solvent, such as hydrochloric acid, which solvent functions not only to form a solvent for the reaction, but also to reduce the valence of the vanadium compound to a valence of less than 5. For example, a vanadium compound, a copper compound, a tellurium compound, phosphorus compound and alkali metal compound may be dissolved in any order in a suitable reducing solvent and the formation of the complex allowed to take place. Preferably, the vanadium compound is first dissolved in the solvent and thereafter the phosphorus, copper, tellurium and other metal compounds, if any, are added. The reaction to form the complex may be accelerated by the application of heat. The deep blue color of the solution shows the vanadium has an average valence of less than 5. The complex formed is then, without a precipitation step, deposited as a solution onto a carrier and dried. In this procedure, the vanadium has an average valence of less than plus 5, such as about plus 4, at the time it is deposited onto the carrier or precipitated without the carrier. Generally, the average valence of the vanadium will be between about plus 2.5 and 4.6 at the time of the precipitation.

In another method the catalyst is prepared by precipitating the metal compounds, either with or without a carrier, from a colloidal dispersion of the ingredients in an inert liquid. In some instances the catalyst may be deposited as molten metal compounds onto a carrier; however, care must be taken not to vaporize off any of the ingredients such as phosphorus. The catalysts have also been prepared by heating and mixing anhydrous forms of phosphorus acids with vanadium compounds, copper compounds, Me compounds, and the alkali metal compound. The catalysts may be used as either fluid bed or fixed bed catalysts. In any of the methods of preparation, heat may be applied to accelerate the formation of the complex.

A very old and traditional method of obtaining vanadyl chloride as disclosed by Koppel et al, Zeit. anorg. Chem, 45, p. 346–351, 1905 is the reduction of $V_2O_5$ in alcoholic HCl solution. This method has been recommended for the preparation of the phosphorus-vanadium oxidation catalyst for example, by Kerr in U.S. Pat. No. 3,255,211 where the solvent also serves as the reducing agent. Subsequently, U.S. Pat. No. 4,043,943 employed this method of reducing vanadium to prepare the basic phosphorus-vanadium catalyst, however, catalyst produced in this manner are known to require a very specific activation procedure in order to be useful as catalyst, as described for example, in U.S. Pat. No. 4,017,521.

In an early series of commonly owned patents, a unique group of vanadium-phosphorus, oxidation catalysts, were disclosed, i.e., U.S. Pat. Nos. 3,156,705; 3,156,706; 3,255,211; 3,255,212; 3,255,213; 3,288,721; 3,351,565; 3,366,648; 3,385,796 and 3,484,384. These processes and catalysts proved highly efficient in the oxidation of n-butenes to maleic anhydride. Since the issuance of these pioneer patents, numerous patents have issued with various modifications and improvements over the basic discoveries set forth there, e.g., U.S. Pat. Nos. 3,856,824; 3,862,146; 3,864,280; 3,867,411; 3,888,886; 4,071,539; 4,097,498; 4,105,586; 4,152,338; 4,152,339 and 4,153,577.

In a recently developed procedure disclosed in the commonly assigned U.S. Patent application Ser. No. 047,323 filed June 11, 1979 which is incorporated herein in its entirety, an improved catalyst is that produced from an alcoholic HCl solution reduction of vanadium pentoxide wherein the organic solvent is an alcohol such as isobutyl alcohol and the reduction of the vanadium is obtained by contacting it with HCl. This is conveniently carried out by passing gaseous HCl through the alcohol having the vanadium pentoxide suspended therein. The vanadium pentoxide is reduced by the HCl and brought into solution as the vanadyl chloride. The completion of the reduction is the appearance of a dark reddish brown solution. Hydrogen bromide would be about the same as a reducing agent in this system. It has been found that the reduction temperature should be maintained at no greater than 60° C. and preferably less than 55° C. Optimumly active catalysts are the result when the reduction is carried out at temperatures in the range of about 35° C. to 55° C., preferably 40° to 55° C.

To obtain the mixed oxides of vanadium and phosphorus, phosphoric acid of approximately 99%, $H_3PO_4$ (98 to 101%) is added, for example, prepared from 85 $H_3PO_4$ and $P_2O_5$ or commercial grades of 105 and 115% phosphoric acid diluted with 85% $H_3PO_4$ and the vanadium compound digested, which is discerned by a change in the color of the solution of a dark blue green. Zinc or other catalyst components are conveniently added along with the phosphoric acid. The alcohol is then stripped off to obtain the dried catalyst.

Catalysts have been prepared in various shapes and configurations, for example, saddles, discs, spheres, cylinders, tubes, granules and the like. For example, U.S. Pat. No. 2,078,945 discloses hydrosilicate catalyst may be formed in tubes or solid cylinders, which may then be crushed and screened to provide irregular catalyst shape. U.S. Pat. Nos. 4,178,298 and 4,181,628 both disclose that mixed oxide oxidation catalyst containing vanadium and phosphorus may be employed as pellets, tablets or cylinders. Rounded aggegate having a void center and a single cavity in the external surface communicating to the void center and named amphora is described in U.S. Pat. Nos. 3,848,033; 3,966,639; 4,094,922 and 4,171,454. U.S. Pat. Nos. 4,153,539 and 4,170,569 disclose rounded similar catalysts which has been named amphora II, but having two cavities 180° C. opposed communicating with the hollow center. The amphora II aggregate is described as particularly effective and advantageous in any process in which the feed is present in the reactor partially in the liquid phase.

The production of dicarboxylic acid anhydride by catalytic oxidation of hydrocarbons is well known. The current principal route for the production of maleic anhydride from $C_4$ hydrocarbons has been desirable in the past, but is now even more desirable in view of the particular world shortage of benzene. It can be readily appreciated that direct oxidation of $C_4$ hydrocarbons would be a hydrocarbon conservation, since for each mol of maleic anhydride prepared from benzene, one mol of benzene, molecular weight 78 is consumed, whereas for each mol of the $C_4$, only 54 to 58 mol weight of hydrocarbon is consumed. The benzene process has consistently produced high conversions and selectivities.

A more desirable process for producing maleic anhydride would be a direct oxidation of n-butenes or butadiene. Also, n-butenes may have higher economic petrochemical utilization than the n-butanes, which are now, often wastefully burned as cheap fuel.

Normal butane requires a solid tableted catalyst rather than a support with the catalytic component deposited thereon because of the energy requirements. Due to the high loading necessitated by economics, conversions of butane in excess of 75% have been unobtainable. Higher conversion results in high hot spot temperatures which adversely effect yield.

It is an advantage of the present invention that greater catalyst activity is obtained. It is a further advantage that less weight of catalyst is employed. Another advantage is that lower pressure drop through the reactor is obtained. It is a feature that the reduced pressure drop allows for high flow rates and increased production results. A further advantage is better heat removal from the reactor zone, which allows for higher conversions and greater productivity. These and other advantages and features will become clear from the following description and discussion.

SUMMARY OF THE INVENTION

The present invention is in a novel catalyst structure of a vanadium-phosphorus oxidation catalyst comprising tablets having a hole therethrough. That is the catalyst structure comprises a small cylinder having a bore therethrough. Preferably, the height and diameter of the structure are substantially the same, such that the catalyst is substantially a ring of catalytic material.

The catalyst structures are usually small, i.e., in the range of 5/32 to 3/16 inch diameter and 5/32 to 3/16 inch thickness, or about 2½ to 10 mesh (Tyler Standard). The hole or hollow core through the tablet usually has a diameter of about 30 to 50% of the diameter of the tablet. Preferably, the hole or hollow core is substantially in the center of the tablet, and extends from one face through the tablet to the other face, i.e., the hole is substantially centered on and extends along an axis extending through the center point of the two faces of the tablet.

Because normal butane requires a higher excitation than for example, normal butene, it has been found that the catalyst structure consists essentially of catalytic material, that is fillers, extenders, supports and the like are not employed in these structures, although conventional binders, such as polyvinyl alcohol may be used to strengthen the catalyst structures. Only as much binder as is necessary would be used and preferably none would be employed (the structure is preferably solid catalytic material) although the catalyst structure consists essentially of catalytic material the catalytic material may have the variations described herein.

DETAILED DESCRIPTION OF PREFERRED EMBODIMENTS

Figure 1:
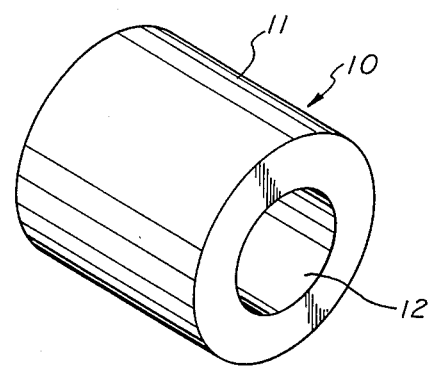
FIG. 1 is a perspective view of a catalyst structure according to the present invention.

The catalytic material from which the catalyst structure is made is a vanadium-phosphorus-oxygen complex type catalyst for the conversion of hydrocarbons to the corresponding anhydride in which the catalyst usually contains at least one modifying component, Me, which is a metal (including the rare earth metals) an alkali, alkaline earth metal, or mixture thereof.

The precise structure of the present complex catalyst has not been determined; however, the complex may be represented by formula $$VP_aMe_bO_x$$

wherein Me is the modifying component, a is 0.90 to 1.3, b is 0.001, preferably 0.005 to 0.4. The representation is not an empirical formula and has no significance other than representing the atom ratio of the active metal components of the catalyst. The x, in fact, has no determinate value and can vary widely, depending on the combinations within the complex. That there is oxygen present is known and the $O_x$ is representative of this.

The Me component as well as the base composition and ratios of components are all well known as described in infinite detail in the art noted above. The composition of the catalytic component is not the subject of the present invention although it is an integral part of the invention which is the discovery that the particular structure of the pelleted composition produces startlingly superior results in its use for the partial oxidation of normal butane to produce maleic anhydride.

Among the various Me components which have been used either alone or in combination with each other are metal and metaloids from Groups Ia, Ib, IIa, IIb, IIIa, IIIb, IVa, IVb, Va, the 4th period of VIIIb, and the rare earths of the Periodic Table of elements. Some specific Me components are Cu, Ag, Zn, Cd, Al, Ga, In, Sc, Y, La, Ge, Sn, Pb, Ti, Zr, Sb, Bi, As, Fe, Co, Ni, Ce, Pr, Nd, Cr, Li, Na, K, Rb, Fr, Nb, Te, W, Pd, Mn, Mo, Re, Sm, Hf, Ta, Th, U, Sn, B, Si, Mg, Ba, Tb and Eu.

The Me components are variously described as stabilizers, promoters, modifiers or the like. Regardless of the characterization the Me components are a part of the catalyst, in that they effect the performance thereof in the oxidation of hydrocarbons.

In regard to normal butanes some more preferred Me components are Cu, Mo, Ni, Co, Cr, Nd, Ce, Ba, Y, Sm, Te, Zr, W, Pd, Ag, Mn, Zn, Re, La, Hf, Ta, Th, U, Eu, Nb, Ru, Li, Mg, B and Si.

Although the catalyst may be produced with carriers or diluents, it is not preferable or desirable to do so since a normal butane requires a greater excitation, than for example n-butene. Hence, the present hollow core tablet is substantially a solid structure of the catalytic material with the exception of binders used in the tableting procedure. The presence of carriers or diluents will not effect the structure, but such a catalyst would not be of value because of low yield and productions. It can be readily appreciated that the presence of the greatest number of active catalytic sites on the catalyst structure is the desirable condition for a butane oxidation catalyst.

Although the catalyst structure of the present invention is described as a tablet having a hole or a hollow core tablet, it could just as well be a extruded hollow core structure cut into short sections, having substantially the same configuration as the tableted material.

Some of the more effective catalysts in terms of productivity and stability are those with few components in addition to P-V-O such as Zn, Li and/or Si, such as disclosed and noted above in pending application Ser. No. 047,323. The resultant catalyst complex is characterized as a mixed oxide, however, the structure of the complex has not been determined but may be conveniently represented by a formula such as $$V\ P_a Zn_{b'} Si_c Li_d O_x$$

where a is 0.90 to 1.3, b' is 0.005 to 0.2, c is 0 to 0.3 and d is 0 to 0.15. As noted above, this representation is not an empirical formula and has no significance other than representing the atom ratio of the components of the catalyst.

Figure 2:
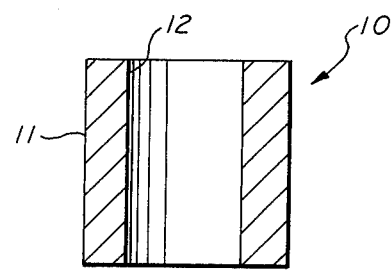
FIG. 2 is a cross sectional elevation of a catalyst structure according to the present invention.
Figure 3:
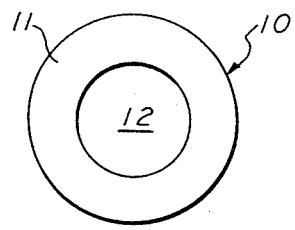
FIG. 3 is an end view of a catalyst structure according to the present invention.

FIG. 1 is a P-V-O n-butane oxidation catalyst 10 according to the present invention which is a cylindrical 11 of the P-V-O catalytic material with a bore 12 therethrough. In FIG. 2, the structure 10, for example a tablet 11 with bore 12 through the center. FIG. 3 shows an end view of the structure 10 with the catalytic material cylinder 11 and bore 12 therethrough.

As described in that process, the organic solvent is preferably a primary or secondary alcohol such as methanol, ethanol, 1-propanol, 2-propanol, butanol, 2-butanol, 2,methyl-1-propanol, 3-methyl-2-butanol, 2,2-dimethyl-1-propanol, 1-hexanol, 4-methyl-1-pentanol, 1-heptanol, 4-methyl-1-hexanol, 4-methyl-1-heptanol, 1,2-ethanediol, glycerol, trimethylolpropane, diethylene glycol and triethylene glycol. The alcohol is also a mild reducing agent for the vanadium +5 compound.

It has been found that lower ratios of zinc/vanadium produce the most active catalyst and compositions containing Zn/V mole ratio in the range of 0.01 to 0.07 are preferred.

The phosphorus is generally present in these catalysts as well as those of the prior art in the mole ratio of P/V 0.09–1.3/1. Optimum ratios P/V are found to be below 1.22/1 and above 1.0/1.

The point at which the zinc component, lithium component and/or silicon component or other beneficial additives are added is not critical so long as they are present prior to formation of the solid catalyst precipitate. This is conveniently done along with the phosphoric acid addition, thereby assuring the intimate mixing of the catalyst components.

The modifier components are added as the compounds thereof such as acetates, carbonates, chlorides, bromides, oxides, hydroxides, phosphates and the like e.g., zinc chloride, zinc oxide, zinc oxalate, lithium acetate, lithium chloride, lithium bromide, lithium carbonate, lithium oxide, lithium ortho phosphate, tetra ethyl ortho silicate, silicon tetra chloride, or other organo silones.

The use of this class of catalytic material (as broadly and specifically disclosed) for the partial oxidation of $C_4$–$C_{10}$ hydrocarbons to the corresponding anhydrides is generally recognized. They have been widely considered for the conversion of normal $C_4$ hydrocarbons, both the alkane, n-butane, and alkene, n-butene, for the production of maleic anhydride, which has a wide commercial usage.

The oxidation of the n-$C_4$ hydrocarbon to maleic anhydride may be accomplished by contacting, e.g., n-butane in low concentrations in oxygen with the described catalyst. Air is entirely satisfactory as a source of oxygen, but synthetic mixtures of oxygen and diluent gases, such as nitrogen, also may be employed. Air enriched with oxygen may be employed.

The gaseous feed stream to the standard tubular oxidation reactors normally will contain air and about 0.5 to about 2.5 mol percent hydrocarbons such as n-butane. About 1.0 to about 2.0 mol percent of the n-$C_4$ hydrocarbon are satisfactory for optimum yield of product for the process of this invention. Although higher concentrations may be employed, explosive hazards may be encountered except in fluidized bed reactors where concentrations of up to about 4 or 5 mole % can be used without explosive hazzard. Lower concentrations of $C_4$, less than about one percent, of course, will reduce the total yields obtained at equivalent flow rates and thus are not normally economically employed.

The flow rate of the gaseous stream through the reactor may be varied within rather wide limits but a preferred range of operations is at the rate of about 50 to 300 grams of $C_4$ per liter of catalyst per hour and more preferably about 100 to about 250 grams of $C_4$ per liter of catalyst per hours. Residence times of the gas stream will normally be less than about 4 seconds, more preferably less than about one second, and down to a rate where less efficient operations are obtained. The flow rates and residence times are calculated at standard conditions of 760 mm. of mercury and at 25° C. A preferred feed for the catalyst of the present invention for conversion to maleic anhydride is a n-$C_4$ hydrocarbon comprising a predominant amount of n-butane and more preferably at least 90 mol percent n-butane.

A variety of reactors will be found to be useful and multiple tube heat exchanger type reactors are quite satisfactory. The tubes of such reactors may vary in diameter from about ¼ inch to about 3 inches, and the length may be varied from about 3 to about 10 or more feet. The oxidation reaction is an exothermic reaction and, therefore, relatively close control of the reaction temperature should be maintained. It is desirable to have the surface of the reactors at a relatively constant temperature and some medium to conduct heat from the reactors is necessary to aid temperature control. Such media may be Woods metal, molten sulfur, mercury, molten lead, and the like, but it has been found that eutectic salt baths are completely satisfactory. One such

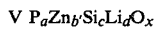

salt bath is a sodium nitrate-sodium nitrite-potassium nitrite eutectic constant temperature mixture. An additional method of temperature control is to use a metal block reactor whereby the metal surrounding the tube acts as a temperature regulating body. As will be recognized by one skilled in the art, the heat exchange medium may be kept at the proper temperature by heat exchangers and the like. The reactor or reaction tubes may be iron, stainless steel, carbon-steel, nickel, glass tubes such as Vycor and the like. Both carbon-steel and nickel tubes have excellent long life under the conditions of the reactions described herein. Normally, the reactors contain a preheat zone of an inert material such as ¼ inch Alundum pellets, inert ceramic balls, nickel balls or chips and the like, present at about one-half to one-tenth the volume of the active catalyst present.

The temperature of reaction may be varied within some limits, but normally the reaction should be conducted at temperatures within a rather critical range. The oxidation reaction is exothermic and once reaction is underway, the main purpose of the salt bath or other media is to conduct heat away from the walls of the reactor and control the reaction. Better operations are normally obtained when the reaction temperature employed is no greater than about 100° C. above the salt bath temperature. The temperature in the reactor, of course, will also depend to some extent upon the size of the reactor and the $C_4$ concentration. Under usual operating conditions, in a preferred procedure, the temperature in the center of the reactor, measured by thermocouple, is about 365° C. to about 550° C. The range of temperature preferably employed in the reactor, measured as above, should be from about 380° C. to about 515° C. and the best results are ordinarily obtained at temperatures from about 390° C. to about 415° C. Described another way, in terms of salt bath reactors with carbon steel reactor tubes about 1.0 inch in diameter, the salt bath temperature will usually be controlled between about 350° C. to about 550° C. under normal conditions, the temperature in the reactor ordinarily should not be allowed to go above about 470° C. for extended lengths of time because of decreased yields and possible deactivation of the catalyst.

The reaction may be conducted at atmospheric, super-atmospheric or below atmospheric pressure. The exit pressure will be at least slightly higher than the ambient pressure to insure a positive flow from the reaction. The pressure of the inert gases must be sufficiently high to overcome the pressure drop through the reactor.

The maleic anhydride may be recovered in a number of ways well known to those skilled in the art. For example, the recovery may be by direct condensation or by adsorption in suitable media, with subsequent separation and purification of the maleic anhydride.

In the following examples, two types of reactors were employed. The results of the tests in the two reactors are qualitatively comparable, i.e., an increase in maleic anhydride yield in the smaller equipment will be reflected in the larger equipment, although the absolute numbers may differ.

"A" REACTORS

The "A" reactors are a 4-tube cylindrical brass block (8" O.D.×18") reactor made of alloy 360. The block was heated by two 2500 watt (220 volt) cartridge heaters controlled by means of a 25 amp. thermoelectric proportional controller with automatic reset. Prior to its insulation, the block was tightly wound with a coil by ⅜" copper tubing. This external coil was connected to a manifold containing water and air inlets for cooling of the reactor block. The reactors were made of a 304 stainless steel tube, 1.315" O.D. and 1.049" I.D., 23½" long, containing a centered ¼" O.D. stainless steel thermocouple well. The lower end of the reactor was packed with a 1" bed of 3 mm pyrex beads. The next 12" of the reactor were packed with catalyst (5/32"×5/32" tablets with 1/16" I.D. hole through the center of each tablet (designated as hollow) in one reactor and the same catalytic material in a 5/32"×5/32" tablet without a hole (designated solid) for comparison) followed by about a 10" bed of 3 mm pyrex beads. The gas streams are separately metered into a common line entering the top of the reactor. The reaction vapors are passed through two 2000 ml. gas scrubbing bottles containing 800 ml. of water. The vapors from the scrubbers then go through a wet test meter and are vented. The inlet gases are sampled before entering the reactor and after the water scrubbers. The feed was 0.7 to 0.8 mol % $C_4$, e.g., n-butane, in air at 2300 $hr^{-1}$ GHSV for both reactors such that the same conditions of feeding reactant existed in both reactors. Since the reaction is exothermic, the reactor temperature, is a function thereof.

The inlet gases and water scrubbed outlet gases were analyzed by gas chromatography using the peak area method. Butane, carbon dioxide and any olefins or diolefins present in the gas streams were determined using a ¼" column with a 5' foresection, containing 13 wt.% vacuum pump oil on 35/80 mesh chromosorb, followed by a 40' section containing 26 wt.% of a 70/30 volume ratio of propylene carbonate to 2,4-dimethylsulfolane on 35/80 mesh chromosorb. The analysis was conducted at room temperature with hydrogen as the carrier gas (100 ml/minute). Carbon monoxide was analyzed on a ¼" column with a 3' foresection of activated carbon followed by a 6' section of 40/50 mesh 5 A molecular sieves. This analysis was run at 35° C. with helium as the carrier gas (20 psi).

The water scrub solutions were combined and diluted to 3000 ml. in a volumetric flask. An aliquot of this solution was titrated with 0.1 N sodium hydroxide solution to determine maleic acid (first end point) and weak acids in solution and titrated to determine the carbonyls, using hydroxylamine hydrochloride. The results are reported in the Table.

"B" REACTOR

The "B" Reactors are 12 foot tubes of 1 inch diameter employed 950 milliliters of catalyst packed with inert 12 inches of ¼ inch Alundum pellets on top of the catalyst material and 6 inches of Alundum pellets below the catalyst.

Two columns are packed with catalytic material, which in one column was 5/32"×5/32" tablet with a 1/16" I.D. hole through the center of each tablet (hollow) and in the other contained the same catalytic material in a 5/32"×5/32" tablet without the hole (solid).

The reactors were encased in a 7% sodium nitrate −40% sodium nitrate −53% potassium nitrite eutectic mixture constant temperature salt bath. The reactor was slowly warmed to 400° C. (250° C.-270° C. air passing over catalyst) while passing a gas stream containing 0.5 to 0.7 mol percent n-butane and air over the catalyst beginning at about 280° C. The reactor outlet was maintained at 1 psig. After the reactor had reached 400° C., the catalyst was aged by passing the n-butane-air mixture therethrough for 24 hours. The n-butane-air and temperature was increased to obtain 80-90% conversion. The salt bath is in operation at a maximum of 425° C. The maximum throughput is achieved in relation to the maximum salt bath temperature and maximum hot spot of about 450° C. The hot spot is determined by a probe through the center of the catalyst bed. The temperature of the salt bath can be adjusted to achieve the desired relationship between the conversion and flow rates of the n-$C_4$-air mixture. A Gas Hourly Space Velocity (GHSV) of 2500 hr$^{-1}$ was employed, feeding the same mole % $C_4$ feed to both reactors. The exit gases were cooled to about 55°-60° C. at about ½ psig. Under these conditions, about 30-50% of the maleic anhydride condenses out of the gas stream. A water scrubber recovery and subsequent dehydration and fractionation were used to recover and purify the remaining maleic-anhydride in the gas stream after condensation. The combined maleic anhydride recovered is purified and recovered at a temperature of about 140°-150° C. overhead and 145° C. bottom temperatures in a fractionator. The purified product had a purity of 99.9+ percent maleic anhydride.

The A reactors provide a relative indication of the results of the salt bath tubes (B reactors) which are intended to reflect a full scale operation.

The results of the two comparative runs are set out below in the TABLE.

The following typical catalyst preparative procedures illustrate typical catalyst work up using the information discussed above.

CATALYST PREPARATION

Into a 5 liter glass reactor was charged 1.8 liters of anhydrous isobutyl alcohol and 318 g. of vanadium pentoxide. The reactor was equipped with overhead stirrer, gas inlet, thermowell and a Dean Stark trap with water condensor. Approximately 3.5 lbs. of HCl gas were passed through the stirred suspension at a rate as to maintain a reaction temperature of about 50° C. To the resulting dark reddish brown solution was added an alcoholic solution of 99.3% phosphoric acid previously prepared by adding 117.2 g. of $P_2O_5$ to 302.58 g. of 85% $H_3PO_4$ until solution was complete and then diluting the acid with 420 ml of anhydrous alcohol. Zinc chloride (4.77 grams) and lithium chloride (0.47 grams) were added in the phorphoric acid solution. The resulting solution was refluxed for 2.0 hours. Effluent gases were scrubbed with a caustic solution. At the end of the digestion period, the alcohol was stripped until about 1.8 liters were recovered from the dark blue solution. The resulting slurry was dried at 150° C. The dried powder was formed into 5/32"×5/32" tablets and some having 1/16" I.D. holes struck therein according to the present invention.

The catalyst is conditioned for use by placing the catalyst tablets in the tubular reactor of a fixed bed reactor and carrying out the conditioning as described above. The reactor (B) is heated by the salt bath.

The C, S and Y used in reporting reaction results have the following meaning and relationship—C (conversion)×S (selectivity)=Y (yield). MAN is abbreviation of maleic anhydride.

TABLE

| Ex. | "A" Reactor Brass Block Tablet | Reactor Temp., °C. | % Conversion | Mole % MAN Selectivity | Yield | Wt. % Yield MA |
|---|---|---|---|---|---|---|
| 1 | Hollow | 380 | 78.7 | 65.4 | 51.5 | 87 |
| 2 | Solid | 402 | 73.9 | 56.3 | 41.5 | 70.2 |

| | "B" Reactors | Temp., °C. | | Mole % | % | Mole % MAN | | Wt. % |
|---|---|---|---|---|---|---|---|---|
| Ex. | Tablet | Salt | Hot Spot | $C_4$ Feed | Conversion | Selectivity | Yield | Yield MA |
| 3 | Hollow | 408 | 447 | 1.70 | 82.5 | 67.8 | 55.9 | 94.5 |
| 4 | Solid | 386 | 447 | 1.69 | 75.2 | 67.1 | 50.5 | 85.3 |
| | Increasing conversion level of solid system gave the following results: | | | | | | | |
| 5 | Solid | 388 | 460 | 1.72 | 79.5 | 56.5 | 44.9 | 75.9 |

The data shows that in both types of reactors under the same conditions of air and $C_4$ feed (for the reactor pairs) the catalyst structure according to the present invention produced higher conversions and higher selectivity. In the case of the commercial reactor tube type pilot plant ("B" Reactor) the yield was a surprising 5% absolute greater using the present hollow core catalyst and the unit productivity was over 9 wt.% greater.

When the conversion of the solid prior art catalyst was increased, the selectivity to maleic anhydride (MA) dropped substantially.

It should be appreciated that illustrative examples employing a specific catalytic material for convenience and other V-P-O catalyst having different modifiers will show the same relative performance between the present hollow core structures and the prior art solid catalyst.

The invention claimed is:

1. A normal butane partial oxidation catalyst structure comprising a cylinder having a bore therethrough, said cylinder consisting essentially of catalytic material, which is comprised of a phosphorus, vanadium, oxygen complex.

2. The normal butane partial oxidation catalyst structure according to claim 1 wherein said complex contains V, P and Me in a atomic ratio of V:P:Me of 1:0.90 to 1.3:0.001 to 0.4, Me is a metal, alkali metal, alkaline earth metal or mixture thereof.

3. The normal butane partial oxidation catalyst structure according to claim 2 wherein Me is Cu, Ag, Zn, Cd, Al, Ga, In, Sc, Y, La, Ge, Sn, Pb, Ti, Zr, Sb, Bi, As, Fe, Co, Ni, Ce, Pr, Nd, Cr, Li, Na, K, Rb, Fr, Nb, Te, W, Pd, Mn, Mo, Re, Sm, Hf, Ta, Th, U, Sn, B, Si, Mg, Ba, Tb, Eu or mixtures thereof.

4. The normal butane partial oxidation catalyst structure according to claim 3 wherein Me is Cu, Mo, Ni, Co, Cr, Nd, Ce, Ba, Y, Sm, Te, Zr, W, Pd, Ag, Mn, Zn, Re, La, Hf, Ta, Th, U, Eu, Nb, Ru, Li, Mg, B, Si or mixtures thereof.

5. The normal butane partial oxidation catalyst structure according to claim 4 where Me is Zn, Si, Li or a mixture thereof.

6. The normal butane partial oxidation catalyst structure according to claim 1, 2, 3, 4 or 5 wherein said cylinders are in the range of 2 ½ to 10 mesh.

7. The normal butane partial oxidation catalyst structure according to claim 6 where said bore is about 30 to 50% of the diameter of said cylinder.

8. The normal butane partial oxidation catalyst structure according to claim 7 wherein said bore is substantially centered through said cylinder.

9. The normal butane partial oxidation catalyst structure according to claim 6 wherein the height and diameter of said structure are substantially the same.

* * * * *